United States Patent [19]

Hoffman

[11] 4,009,207
[45] Feb. 22, 1977

[54] CARBAMOYLALKYL SUBSTITUTED POLY(PHOSPHINE OXIDE) FLAME-RETARDANTS

[75] Inventor: Joseph Adrian Hoffman, Somerville, N.J.

[73] Assignee: American Cyanamid Company, Stamford, Conn.

[22] Filed: Apr. 15, 1976

[21] Appl. No.: 677,338

Related U.S. Application Data

[62] Division of Ser. No. 603,463, Aug. 11, 1975, Pat. No. 3,976,685.

[52] U.S. Cl. .................. 260/558 A; 106/15 FP; 252/8.1; 260/45.7 P; 260/558 R; 260/561 P
[51] Int. Cl.² .......................................... C07C 103/75
[58] Field of Search ................. 260/558 A

[56] References Cited

UNITED STATES PATENTS

| | | | |
|---|---|---|---|
| 3,284,543 | 11/1966 | Gillham et al. .................. | 260/887 |
| 3,322,861 | 5/1967 | Gillham et al. ............... | 260/45.7 X |
| 3,895,048 | 7/1975 | Hoffman ....................... | 260/465 H |

FOREIGN PATENTS OR APPLICATIONS 1,405,747  5/1965  France ........................... 260/558 A

OTHER PUBLICATIONS

Ismagilov et al., CA 77:126773n (1972).

*Primary Examiner*—Daniel E. Wyman
*Assistant Examiner*—Thomas A. Waltz
*Attorney, Agent, or Firm*—Frank M. Van Riet

[57] ABSTRACT

Compounds having the formula

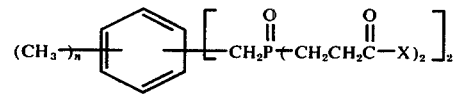

wherein X is OH or $NH_2$ and n is a whole, positive integer of from 1–4, inclusive.

5 Claims, No Drawings

CARBAMOYLALKYL SUBSTITUTED POLY(PHOSPHINE OXIDE) FLAME-RETARDANTS

CROSS-REFERENCE TO RELATED APPLICATIONS

This application is a division of my copending application Ser. No. 603,463, filed Aug. 11, 1975, now U.S. Pat. No. 3,976,685.

This application is related to Application, Ser. No. 603,464 filed Aug. 11, 1975, and directed to polyolefins and polyesters containing the above compounds.

BACKGROUND OF THE INVENTION

The use of alkylenebis(phosphine oxides) to provide flame-retardance to thermoplastic polymers is known, see U.S. Pat. No. 3,284,543, as is the use of cyano-substituted arylenepoly(phosphine oxides), see U.S. Pat. No. 3,895,048. The alkylene compounds are, however, effective only at relatively high concentrations, e.g., 20–25% for most polymers. Additionally, the carboxyalkyl and carbamoylalkyl derivatives of the alkylene compounds are relatively incompatible with non-polar polymers, such as polypropylene, as are many other of said alkylene compounds, at concentrations ranging upward from about 10%, by weight. As a result, most of the alkylene compounds are extremely difficult to incorporate into said non-polar polymers by conventional extrusion and injection molding techniques since they tend to exude from or form a two-phase system in the polymer. Consequently, uniform dispersions of the flame-retardant additives in the polymers are difficult to obtain.

Another disadvantage, sometimes more serious, is the relatively high water-solubility of the alkylene compounds which, in certain applications, such as in dishwasher and clotheswasher components, tends to cause the compounds to be more readily extracted from the polymer. As a result, the polymers then become more flammable and ultimately fail to pass the Underwriter's Laboratory Test of acceptable flame-retardance.

The need for additional compounds which will function in an acceptable flame-retarding manner in non-polar polymers is therefore readily apparent.

SUMMARY OF THE INVENTION

I have now discovered that the above defects of the aforementiond alkylenebis(phospine oxides) can also be overcome, and excellent flame-retardant properties attained, by incorporating into polyolefins and polyesters a compound conforming to Formula I, below. These novel compounds impart excellent flame-retardance to polyolefins and polyesters at relatively low concentrations, are easily incorporated into the polymers to provide stable dispersions and do not leach out of the polymer when it is used in conjunction with water after having been formed into a particular article of manufacture.

DESCRIPTION OF THE INVENTION INCLUDING PREFERRED EMBODIMENTS

The compounds found to be effective in flame-proofing polyolefins, particularly, polypropylene and polyesters, according to the present invention, conform to the formula

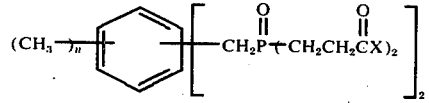

wherein X is OH or NH$_2$ and n is a whole, positive integer of from 1–4, inclusive.

Among the preferred carboxyethyl and carbamoylethyl compounds conforming to Formula I are the following:

1,4-bis[bis(2-carboxyethyl)phosphonylmethyl]-2-methylbenzene;
1,4-bis[bis(2-carboxyethyl)phosphonylmethyl]-2,5-dimethylbenzene;
2,4-bis[bis(2-carboxyethyl)phosphonylmethyl]-1,3,5-trimethylbenzene;
1,4-bis[bis(2-carboxyethyl)phosphonylmethyl]-2,3,5,6-tetramethylbenzene;
1,4-bis[bis(2-carbamoylethyl)phosphonylmethyl]-3-methylbenzene;
1,4-bis[bis(2-carbamoylethyl)phosphonylmethyl]-2,5-dimethylbenzene;
2,4-bis[bis(2-carbamoylethyl)phosphonylmethyl]-1,3,5-trimethylbenzene;
1,4-bis[bis(2-carbamoylethyl)phosphonylmethyl]-2,3,5,6-tetramethylbenzene; and the like.

These componds may be readily prepared by reacting bis(2-carboxyethyl)phosphine oxide or bis(2-carbamoylethyl)phosphine oxide with the appropriately substituted halomethyl benzene in accordance with the general equation:

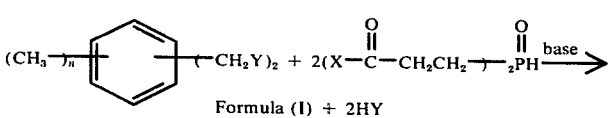

Formula (I) + 2HY wherein Y is a halogen and n + X are as described above.

The intermediate halomethylated benzene compounds may be prepared by reacting the corresponding benzene compound with formaldehyde and a hydrogen halide as disclosed in U.S. Pat. Nos. 2,945,894; 2,951,100; 2,973,391 and 3,069,480. Alternatively, chlorination of the alkyl group or groups of the appropriate methylbenzenes in the presence of a suitable catalyst (see U.S. Pat. No. 2,926,202) or with chlorine absorbed on zeolite (see U.S. Pat. No. 2,956,084) may be carried out.

My novel compounds may also be prepared by conducting derivative reactions on the appropriate 2-cyanoethyl analog, for example, by hydrolysis of the nitrile to the carboxylic acid, esterification of the carboxylic acid and ammonolysis of the ester to the amide. The appropriate 2-cyanoethyl analogs are readily obtained in accordance with the procedures described in said U.S. Pat. No. 3,895,048. Nitrile hydrolysis is achieved by reacting the 2-cyanoethyl compound with an acid, such as hydrochloric acid; at reflux temperature for from 16–36 hours. Hot water is then added, the resultant reaction mixture is cooled to about room temperature, filtered, water washed, dried and recovered as the corresponding acid.

Esterification of the acid to the ester can be accomplished with an alkanol of 1–8 carbon atoms, e.g., methanol in the presence of an aromatic solvent such as benzene and a small amount of an acid such as sulfuric acid. The reaction media containing these reactants are heated at reflux until a complete solution is formed, i.e., 2 – 10 hours, and then heated for an additional 4 – 8 hours. The resultant solution is then cooled and neutralized with a basic material such as sodium bicarbonate. The solution is then filtered and the filtrate is cooled to about 0°–32° F., stirred, filtered again, washed with alcohol and dried.

As mentioned above, the ester can then be used to produce the novel carbamoyl compounds of the present invention. Ammonolysis of the ester can be accomplished by adding to the ester an excess of concentrated aqueous ammonia at 0°–20° C. with stirring for 1–4 hours. The mixture is allowed to come to room temperature and is stirred at that temperature for an additional 32–60 hours. The carbamoyl derivative is recovered by filtration, water washing and drying.

My novel flame-retardant compounds may be incorporated into the polymer by any known means such as, for example, Banbury mixing, extrusion, injection molding etc. in concentrations ranging from about 2 to about 20%, by weight, based on the weight of the polymer to which it is added. Incorporation of the flame-retardant may also be effected during the polymer production, e.g., by adding it to the monomer mixture undergoing polymerization.

The polymers into which my novel flame-retardant compounds may be incorporated include the polyolefins, i.e., polymers produced from ethylene, propylene, especially the homopolymers thereof, e.g., polyethylene, polypropylene and the like. Additionally, I may also use such polymers as the linear aromatic polyesters such as polyethylene terephthalate, polybutylene terephthalate, poly(1,4-cyclohexanedimethylene)terephthalate and the like.

The instant flame-retardant compounds may be utilized as such or in conjunction with various flame-retardant additives such as the ammonium polyphosphates, see col. 3, lines 25–57 of U.S. Pat. No. 3,835,119, hereby incorporated herein by reference, in the ratio of carboxy or carbamoyl derivative to ammonium polyphosphate of 1 : 1 to 1 : 3. Additionally, to the ammonium polyphosphate-carbamoyl or carboxy derivative mixture may be added a metal oxide such as titanium dioxide in amounts ranging from about 0.5 to 5.0 percent, by weight, based on the weight of the polymer. These metal oxides perform synergistically with the ammonium polyphosphate and carboxy or carbamoyl derivative to minimize dripping of the polymer to which they are added when it is burning and before it extinguishes itself, as can be readily appreciated from a perusal of the above 3,835,199 patent.

Various other additives may also be added to the instant flame-retarded compositions such as plasticizers, pigments, fillers, stabilizers, i.e., antioxidants etc., antistatic agents, dyes, photochromics and the like.

The following examples are set forth for purpose of illustration only and are not to be construed as limitations on the present invention except as set forth in the appended claims. All parts and percentages are by weight unless otherwise specified.

EXAMPLE 1

PREPARATION OF 1,4-BIS[BIS(2-CARBOXYETHYL)PHOSPHONYLMETHYL]-2,3,5,6-TETRAMETHYLBENZENE

To 1 liter of concentrated hydrochloric acid are added 103 parts of 1,4-bis[bis(2-cyanoethyl)phosphonylmethyl]-2,3,5,6-tetramethylbenzene. The reaction mixture is refluxed for 24 hours and 800 ml. of hot water are than added. The resultant reaction mixture is cooled to 25° C. and the product is filtered, washed with water and dried. The yield is 137 parts of 1,4-bis[bis(2-carboxyethyl)phosphonylmethyl]-2,3,5,6-tetramethylbenzene having a melting point of 265°–267° C.

EXAMPLE 2

PREPARATION OF 1,4-BIS[BIS(2-CARBOXYETHYL)PHOSPHONYLMETHYL]-2-METHYLBENZENE

The procedure of Example 1 is again followed except that the charge material is 1,4-bis[bis(2-cyanoethyl)phosphonylmethyl]-2-methylbenzene. Good yields of the subject compound are recovered.

EXAMPLE 3

PREPARATION OF 1,4-BIS[BIS(2-CARBOXYETHYL)PHOSPHONYL METHYL]-2,5-DIMETHYLBENZENE

Again following the procedure of Example 1, good yields of 1,4-bis[bis(2-carboxyethyl)phosphonylmethyl]-2,5-dimethylbenzene are recovered when the charge 2-cyanoethyl compound thereof is replaced by 1,4-bis[bis(2-cyanoethyl)-phosphonylmethyl]-2,5-dimethylbenzene.

EXAMPLE 4

PREPARATION OF 2,4-BIS[BIS(2-CARBOXYETHYL)PHOSPHONYLMETHYL]-1,3,5-TRIMETHYLBENZENE

When the charged 2-cyanoethyl compound of Example 1 is replaced by 2,4-bis[bis(2-cyanoethyl)phosphonylmethyl]-1,3,5-trimethylbenzene, the subject compound is recovered in a good yield, the same procedure being followed.

EXAMPLE 5

PREPARATION OF 1,4-BIS[BIS(2-CARBAMOYLETHYL)PHOSPHONYLMETHYL]-2,3,5,6-TETRAMETHYLBENZENE

109 Parts of the 1,4-bis[bis(2-carboxyethyl)phosphonylmethyl]-2,3,5,6-tetramethylbenzene of Example 1, 600 ml. of methanol, 100 ml. of benzene and 1 ml. of concentrated sulfuric acid are heated at reflux until complete solution is achieved (4 hrs.) and heating is then continued for an additional 5 hours. The resultant solution is then cooled and 15 parts of sodium bicarbonate are added. The solution is stirred for 30 minutes and filtered. The filtrate is cooled in an ice/acetone bath, stirred for an additional 1-½ hr., filtered, washed with methanol and dried. 111 Parts of 1,4-bis[bis(2-carbomethoxyethyl)phosphonylmethyl]-2,3,5,6-tetramethylbenzene are recovered of 149°–150° C. m.p.

40 Parts of the carbomethoxyethyl compound are then admixed with 300 ml. of concentrated, aqueous ammonia. The mixture is stirred for 2 hours at 10° C. and then allowed to come to room temperature. Stirring at ambient temperature for 48 hours, filtering, washing with water and drying results in the recovery of 30 parts of 1,4-bis[bis(2-carbamoylethyl)phosphonylmethyl]-2,3,5,6-tetramethylbenzene having a melting point of 322° C. dec.

EXAMPLE 6

PREPARATION OF 2,4-BIS(2-CARBAMOYLETHYL)PHOSPHONYLMETHYL]-1,3,5-TRIMETHYLBENZENE

The procedure of Example 5 is again followed except that the starting 2-carboxyethyl compound is 2,4-bis[bis(2-carboxyethyl)phosphonylmethyl]-1,3,5-trimethylbenzene. The carbomethoxyethyl intermediate is recovered and converted to the corresponding carbamoylethyl product.

EXAMPLE 7

PREPARATION OF 1,4-BIS[BIS(2-CARBAMOYLETHYL)PHOSPHONYLMETHYL]-2-METHYLBENZENE

Again following the procedure of Example 5, the subject compound is recovered in a good yield, the charge being the product of Example 2.

EXAMPLE 8

PREPARATION OF 1,4-BIS[BIS(2-CARBAMOYLETHYL)PHOSPHONYLMETHYL]-2,5-DIMETHYLBENZENE

When the product recovered in Example 3 is used as the charge and the procedure of Example 5 is again followed, 1,4-bis[bis(2-carbamoylethyl)phosphonylmethyl]-2,3-dimethyl-benzene is recovered.

EXAMPLE 9

To 80 parts of unstabilized polypropylene are added, by milling at 175° C., 0.1 part of pentaerythrityl tetrakis(3,4-di-t-butyl-4-hydroxyphenyl)propionate, 0.25 part of distearylthiodipropionate (as primary and secondary stabilizers) 10.0 parts of the product in Example 1, above, 10.0 parts of ammonium polyphosphate and 1.0 part of titanium dioxide. The resultant compounded polypropylene composition is molded at 200° C. into test bars 6 inches ×0.5 inch ×0.125 inch and the bars are tested for flammability according to Underwriter's Test (UL)-94 (vertical). The flammability is rated according to the following definitions:

V-0: flame extinguishes in 0–5 seconds; non-dripping or, if dripping, the drippings do not ignite surgical cotton.

V-1: flame extinguishes in 6–25 seconds; non-dripping or, if dripping, the drippings do not ignite surgical cotton.

V-2: flame extinguishes in 0–25 seconds; drips and ignites surgical cotton.

The results are set forth in Table I, below, along with other test results utilizing other compounds and combinations of materials according to the instant invention and flame-retardant additives of the prior art. Comparative results are indicated by the letter (c). The flame-retardant compounds are set forth by reference to the following structural formula:

TABLE I

| EX. | Z | R | FLAME TEST | COMPATIBILITY | EXTRACTABILITY |
|-----|-----|-----|-----|-----|-----|
| 9 | OH | —H₂C—C₆(CH₃)₄—CH₂— (2,3,5,6-tetramethylphenylene) | V-1 | + | + |
| 10 | OH | —H₂C—C₆H₃(CH₃)—CH₂— (methylphenylene) | V-2 | + | + |
| 11 | OH | —H₂C—C₆H₂(CH₃)₂—CH₂— (dimethylphenylene) | V-2 | + | + |
| 12 | OH | —H₂C—C₆H₂(CH₃)₂—CH₂— (dimethylphenylene, isomer) | V-2 | + | + |
| 13 | NH₂ | —H₂C—C₆(CH₃)₄—CH₂— (2,3,5,6-tetramethylphenylene) | V-1 | + | + |
| 14 | NH₂ | —H₂C—C₆H₂(CH₃)₂—CH₂— (dimethylphenylene) | V-1 | + | + |

TABLE I-continued

| EX. | Z | R | FLAME TEST | COMPATIBILITY | EXTRACTABILITY |
|---|---|---|---|---|---|
| 15 | $NH_2$ | (methylbenzyl with CH3) | V-2 | + | + |
| 16 | $NH_2$ | (trimethylbenzyl) | V-2 | + | + |
| 17C | OH | $+CH_2+_{\overline{2}}$ | V-1 | − | − |
| 18C | $NH_2$ | $+CH_2+_{\overline{2}}$ | V-0 | − | − |
| 19C | $OCH_3$ | $+CH_2+_{\overline{2}}$ | V-2 | − | − |
| 20C | $OCH_3$ | (trimethylbenzyl structure) | V-1 | − | − |
| 21C | $OCH_3$ | (pentamethylbenzyl structure) | — | — | — |

(+) = compatible and non-extractable
(−) = incompatible and extractable

EXAMPLES 22–29

When the procedure of Example 9 is again followed except that the ammonium polyphosphate and titanium dioxide are excluded and 15.0 parts of flame-retardant compound are added to 85.0 parts of polypropylene, the following results are achieved.

TABLE II

| Ex. | Flame-Retardant of Ex.No. | Flame-Test** | Compatability | Extractability |
|---|---|---|---|---|
| 22 | 2 | < 3 in | + | + |
| 23 | 4 | " | + | + |
| 24* | 7 | " | + | + |
| 25 | 6 | " | + | + |
| 26 | 1 | " | + | + |
| 27 | 5 | " | + | + |
| 28* | 3 | " | + | + |
| 29 | 8 | " | + | + |

*polyethylene used.
**ASTM D-635 horizontal test.

EXAMPLES 30–41C

The compounds of Table I, above, are incorporated into polyethylene terephthalate by dry blending at 10%, by weight, based on the weight of the polyester. The blends are melted and stirred for 5–6 minutes at 290°–310° C. The resultant mixtures are cooled, ground into a powder and laminated onto fiberglass sheets by compression molding at 600° F. The laminated sheets are cut into strips 2 inches ×6 inches ×0.03 inch and tested according to ASTM D 2863-70, modified to accept the test strips. In this test, the higher the oxygen index (O.I.), the better the flame-retardance. No ammonium polyphosphate or titanium dioxide are used. The results are set forth in Table III, below.

TABLE III

| Ex. | Flame-Retardant of Ex. No. | Oxygen Index | Compatability | Extractability |
|---|---|---|---|---|
| 30 | 9 | 23.0 | + | + |
| 31 | 11 | 23.3 | + | + |
| 32 | 12 | 22.8 | + | + |
| 33 | 13 | 22.0 | + | + |
| 34 | 14 | 23.8 | + | + |
| 35 | 16 | 23.4 | + | + |
| 36C | 17C | 24.0 | + | − |
| 37C | 18C | degrades | | |
| 38C | 19C | 22.0 | − | − |
| 39C | 20C | 23.3 | + | − |
| 40C | 21C | 23.0 | + | − |
| 41C | Control - no additive | 19–20 | | |

(+) and (−) = see Table I

EXAMPLE 42

The procedure of Example 30 is again followed except that the polyester is polybutylene terphthalate. Similar results are achieved.

EXAMPLE 43

The procedure of Example 34 is again followed except that the polyester is poly(1,4-cyclohexanedimethylene) terephthalate. Substantially identical results are recorded.

I claim:

1. A compound having the formula

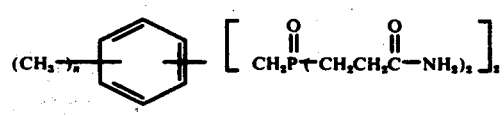

wherein n is a whole, positive integer of 1–4, inclusive.
2. A compound according to claim 1 wherein n is 4.
3. A compound according to claim 1 wherein n is 3.
4. A compound according to claim 1 wherein n is 1.
5. A compound according to claim 1 wherein n is 2.